US006592734B2

United States Patent
Chen

(12) United States Patent
(10) Patent No.: US 6,592,734 B2
(45) Date of Patent: Jul. 15, 2003

(54) SEMI-DRY ELECTROBLOTTER

(75) Inventor: Hui-Wan Chen, Taipei (TW)

(73) Assignee: Wealtec Enterprise Co., Ltd., Taipei (TW)

( * ) Notice: Subject to any disclaimer, the term of this patent is extended or adjusted under 35 U.S.C. 154(b) by 175 days.

(21) Appl. No.: 09/842,853

(22) Filed: Apr. 27, 2001

(65) Prior Publication Data
US 2002/0157953 A1 Oct. 31, 2002

(51) Int. Cl.[7] .................. C02F 1/40; C02F 11/00; C25B 11/00; C25B 13/00; C25B 9/00; G01N 27/27; G01N 27/403; G01N 27/453
(52) U.S. Cl. ..................... 204/614; 204/600
(58) Field of Search .................. 204/614, 600

(56) References Cited

U.S. PATENT DOCUMENTS

| | | | | | |
|---|---|---|---|---|---|
| 3,856,656 | A | * | 12/1974 | Brink ...................... | 204/616 |
| 5,100,626 | A | * | 3/1992 | Levin ...................... | 422/100 |
| 5,217,592 | A | * | 6/1993 | Jones ...................... | 204/614 |
| 5,242,568 | A | * | 9/1993 | Ehr et al. ................ | 204/607 |
| 5,306,468 | A | * | 4/1994 | Anderson et al. ...... | 422/101 |
| 5,571,667 | A | * | 11/1996 | Chu et al. ............... | 435/5 |
| 6,193,868 | B1 | * | 2/2001 | Hsu ........................ | 204/618 |
| 6,203,679 | B1 | * | 3/2001 | Bouis et al. ............ | 204/466 |
| 6,303,389 | B1 | * | 10/2001 | Levin et al. ............ | 436/518 |

* cited by examiner

Primary Examiner—Mark L. Bell
Assistant Examiner—Jennine Brown
(74) Attorney, Agent, or Firm—Bacon & Thomas, PLLC

(57) ABSTRACT

A semi-dry electroblotter for transferring a gel after its electrophoresis onto a membrane enabling the electroblotting process to be efficiently and effectively carried out within a short time, eliminating the shortcomings of the traditional technology, includes an upper block, and a corresponding lower block. A respective positioning member is disposed on each of the lateral sides of the upper block and the lower block, such that the upper block and the lower block will be coupled automatically when they are closed in a correct guiding position. An elastic member and an electrode plate are separately disposed in the interior of the upper block and the lower block, and the elastic member supports the electrode plate so that the electrode plate is biased in a clamping direction. When the gel, membrane, and transfer buffer are placed on the electrode plate in the lower block, and covered with the upper block, and after automatically coupled by the positioning member, the elastic member will provide an appropriate elastic pressure against the electrode plates of the upper block and the lower block to evenly clamp the gel, membrane, and transfer buffer.

3 Claims, 7 Drawing Sheets

SEMI-DRY ELECTROBLOTTER

BACKGROUND OF THE INVENTION

1. Field of the Invention

The present invention relates to a semi-dry electroblotter, and more particularly to a semi-dry, electroblotter for transferring a gel after its electrophoresis onto a membrane enabling the electro-blotting process to be efficiently and effectively carried out within a short time, and eliminating the shortcomings of the traditional technology.

2. Description of the Related Art

The horizontal or vertical immersion tank for electrophoresis is specially designed for the separation and analysis of deoxyribonucleic acid (DNA), ribonucleic acid (RNA), and protein in the biotechnology field. Its principle is to use electric current to drive the molecules to shift on the porous gel. When the molecules shift, they are separated from each other by means of the ionic charge and the size difference of the molecules. Such a process plays a very important role in the application of basic biotechnological theory.

The foregoing gel after electrophoresis forms a molecular mark, and since the molecular mark cannot be stored due to the fragile property of the gel, a semi-dry or a wet blotter is used to transfer the molecular mark onto a membrane in order to attain the purpose of storing the molecular mark for later experiments.

FIG. 1 shows the three-dimensional diagram of the structure of a traditional semi-dry electroblotter, which comprises an upper lid (10) and a lower block (11) of a container; an electrode plate (12) is disposed in the upper lid (10) and the lower block (11) for connecting to the cathode and the anode; a plurality of prewet transfer buffers are being held by the electrode plate (12) of the lower block (11); the gel (14) and the membrane (15) for the transfer are clamped between the plurality of transfer buffers, and the gel (14) is located on top of the membrane (15).

During the transfer, the cathode and the upper lid (10) of the electrode plate (12) form a negatively charged area when electric current is passed, and the anode forms a positively charged area with the electrode plate (12) of the lower block (11). When the upper lid (10) and the lower block (11) are closed, the weight of the upper lid (10) presses the transfer buffers (13), the gel (14), and the membrane (15) to attach to each other. Since the electrons travel from cathode to anode, the molecular marks on the gel can be transferred to the membrane.

FIG. 2 is a three-dimensional diagram showing the structure of another prior-art semi-dry electroblotter. Unlike the foregoing electroblotter, its upper lid (10) has a plurality of knobs (16), and the lower block (11) has a screw column (17). When the transfer buffers, gel, and the membrane are accommodated in sequence between the upper lid (10) and the lower block (11), the user can turn the knob (16) to bolt them to the screw column (17), such that the upper lid (10) and the lower block (11) clamp the transfer buffers, gel, and membrane together, and then the transfer is carried out by applying electric current to them as described above.

Although the foregoing two traditional semi-dry electroblotters can transfer the molecular mark, the gel (14) is fragile, the thickness of the DNA and RNA gel being about 8 mm–10 mm, and that of the protein being just 0.7 mm~1.5 mm. The difference of the thickness between the two is large. Furthermore, the force of clamping the transfer buffers (13), gel (14), and membrane (15) by the two traditional semi-dry electroblotters cannot be controlled. Therefore, overpressing the upper lid (10) occurs frequently during the transfer, which will damage the gel (14) between the upper lid (10) and the lower block (11), cause the whole process to fail. On the other hand, if the force between the upper lid (10) and the lower block (11) is not enough, it will easily produce an air bubble between the gel (14) and the membrane (15), which gives rise to poor conductivity because the attachment is not tight enough, and incomplete transfer of the molecular mark.

Additionally, there is another conventional wet electroblotter (as shown in FIG. 3), which comprises transfer buffers (13), gel (14), and membrane (15) disposed inside a container (20). The container (20) is placed in the solution tank (30), and the cathode and anode of the electrodes are introduced to proceed with the transfer operation.

The wet electroblotter can attain the purpose of a transfer, but the container (20) for accommodating the transfer buffers (13), gel (14), and membrane (15) must be immersed completely into the solution tank (30). The operation and application are therefore inconvenient, and the voltage for the transfer cannot be too large, or else it may evaporate the solution and affect the experiment. Therefore it takes a relatively long time for the wet electroblotters to complete the transfer.

In view of the above shortcomings of the traditional electroblotters, they still need to be improved. In order to provide a more convenient way of performing the transfer operation, the present inventor actively performed research and development in the biotechnological equipment area and with years of practical experience of sales and marketing has developed an electroblotter that is more convenient, reliable, fast and practical than the conventional electroblotter, and yet that ensures the integrity of the gel.

SUMMARY OF THE INVENTION

Generally speaking, the electroblotter of the present invention comprises an upper block, and a corresponding lower block. A corresponding positioning member is disposed on each of the lateral sides of the upper block and the lower block, such that the upper block and the lower block will be coupled automatically when they are closed in a correct guiding position. An elastic member and an electrode plate are separately disposed in the interior of the upper block and the lower block, and the elastic member supports the electrode plate so that the electrode plate has an elastic reaction on the opposite direction when the electrode plate is pressed.

The primary objective of the present invention is to provide an electroblotter which applies an appropriate elastic pressure to the electrode plate using the above-mentioned elastic member to evenly clamp the gel, membrane, and the transfer buffers by means of the electrode plate of the upper block and the lower block in order to solve the incomplete transfer problem for the electroblotting process. Furthermore, since the electrode plate evenly holds the gel, membrane, and transfer buffers by the elastic member, it will not damage the gels easily even they are of different thicknesses.

Another objective of the present invention is provide an electroblotter which can increase the stability of coupling the upper block and the lower block by automatically guiding and latching the corresponding sides of the two blocks when they are closed in order to avoid damage to the gel caused by the manual operation. After the transfer, the upper block is pressed evenly to release the latching of the positioning member, and by means of the elasticity of the foregoing elastic member, the upper block and the lower block can be separated for quick disassembling or cleaning. It offers a very convenient operation for users.

To make it easier for our examiner to understand the objective of the invention, its structure, innovative features, and its performance, we use a preferred embodiment together with the attached drawings for the detailed description of the invention.

BRIEF DESCRIPTION OF THE DRAWINGS

Other objects, features, and advantages of the invention will become apparent from the following detailed description of the preferred but non-limiting embodiment. The description is made with reference to the accompanying drawings, in which.

DETAILED DESCRIPTION OF THE PREFERRED EMBODIMENTS

Figure 1:
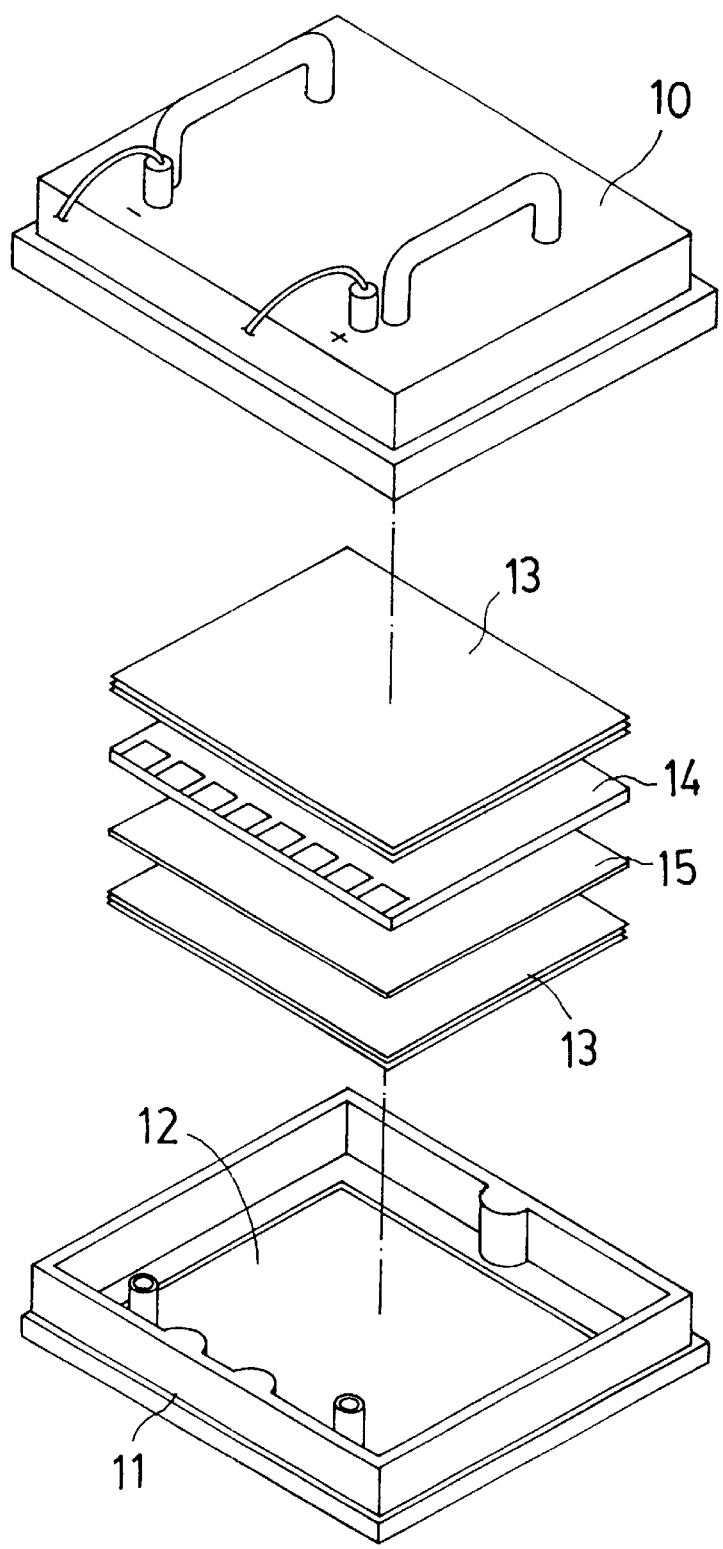
FIG. 1 shows the three-dimensional structure of a prior-art semi-dry electroblotter.
Figure 2:
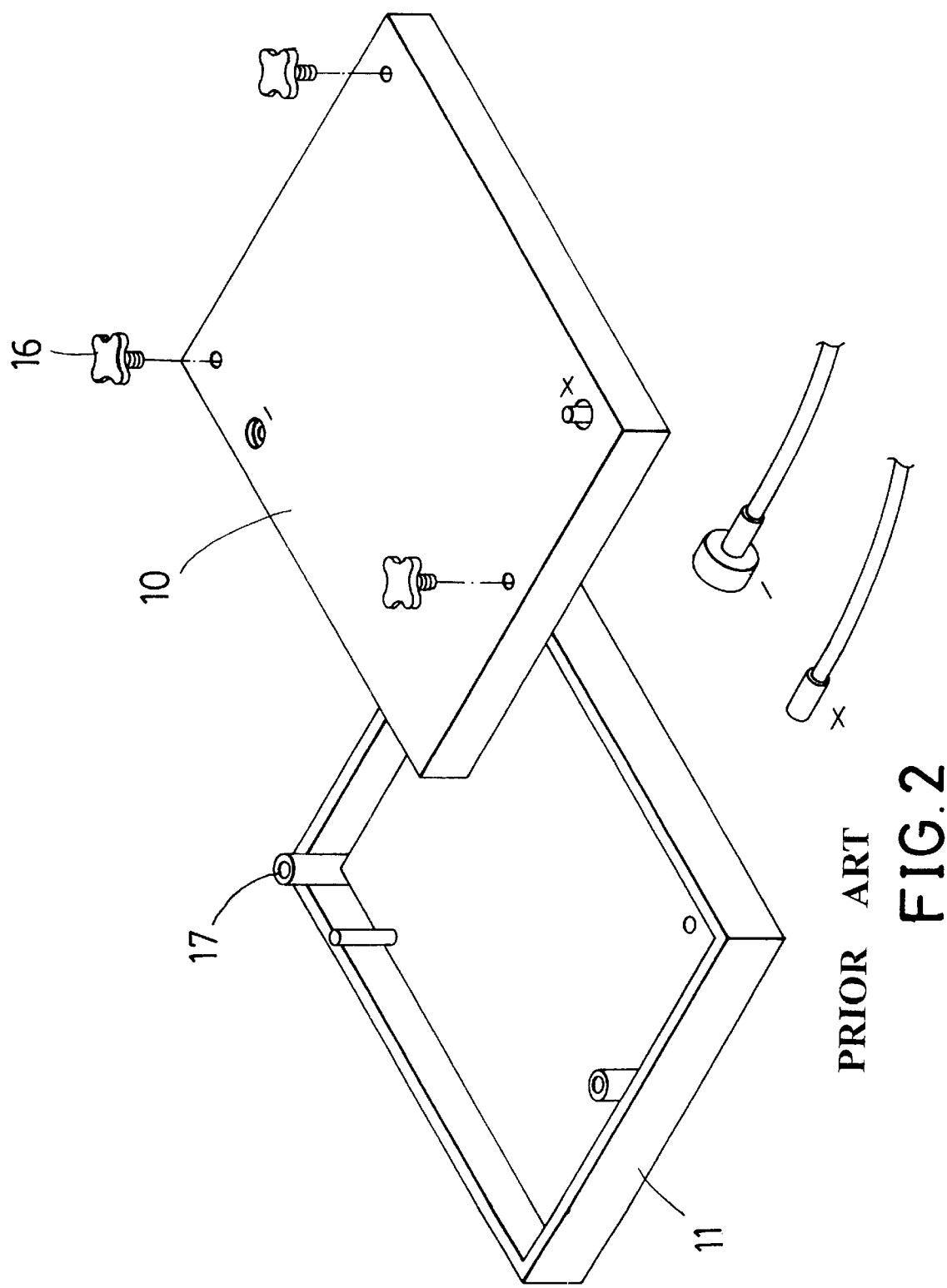
FIG. 2 shows the three-dimensional structure of another prior-art semi-dry electroblotter.
Figure 3:
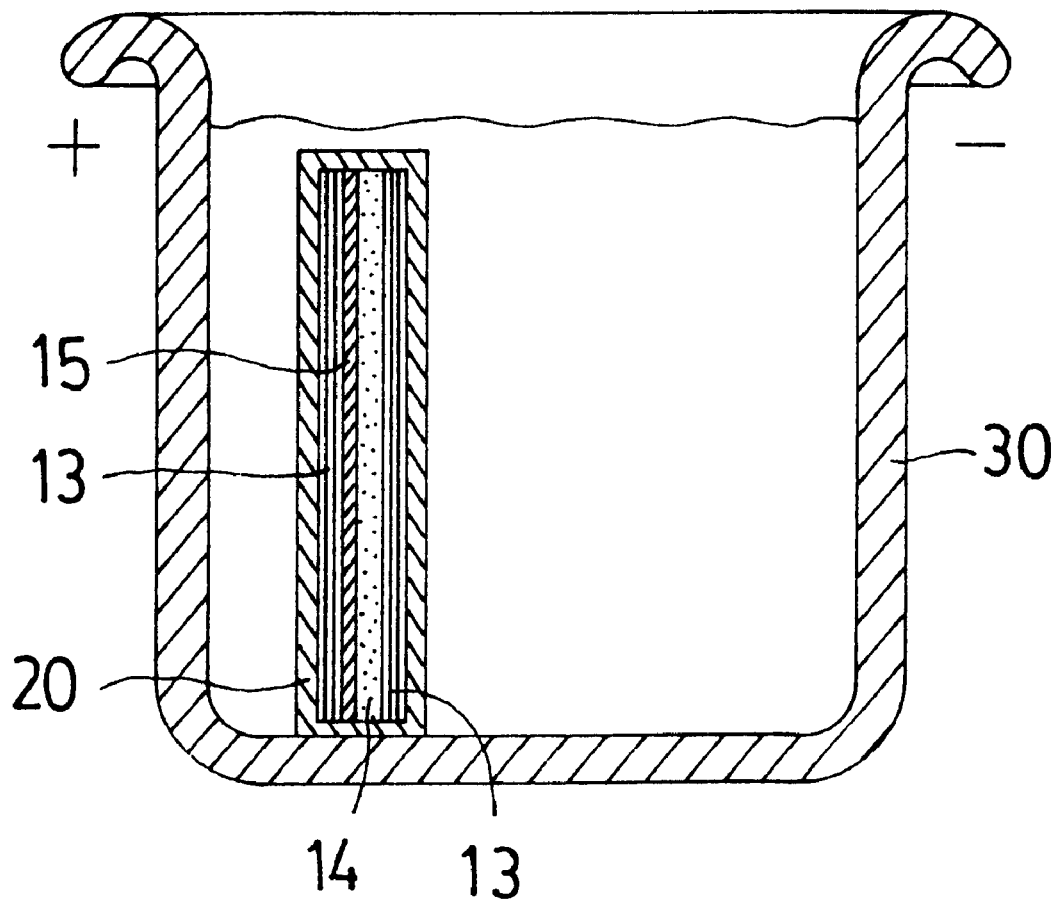
FIG. 3 shows the schematic diagram of a prior-art wet electroblotter.
Figure 4:
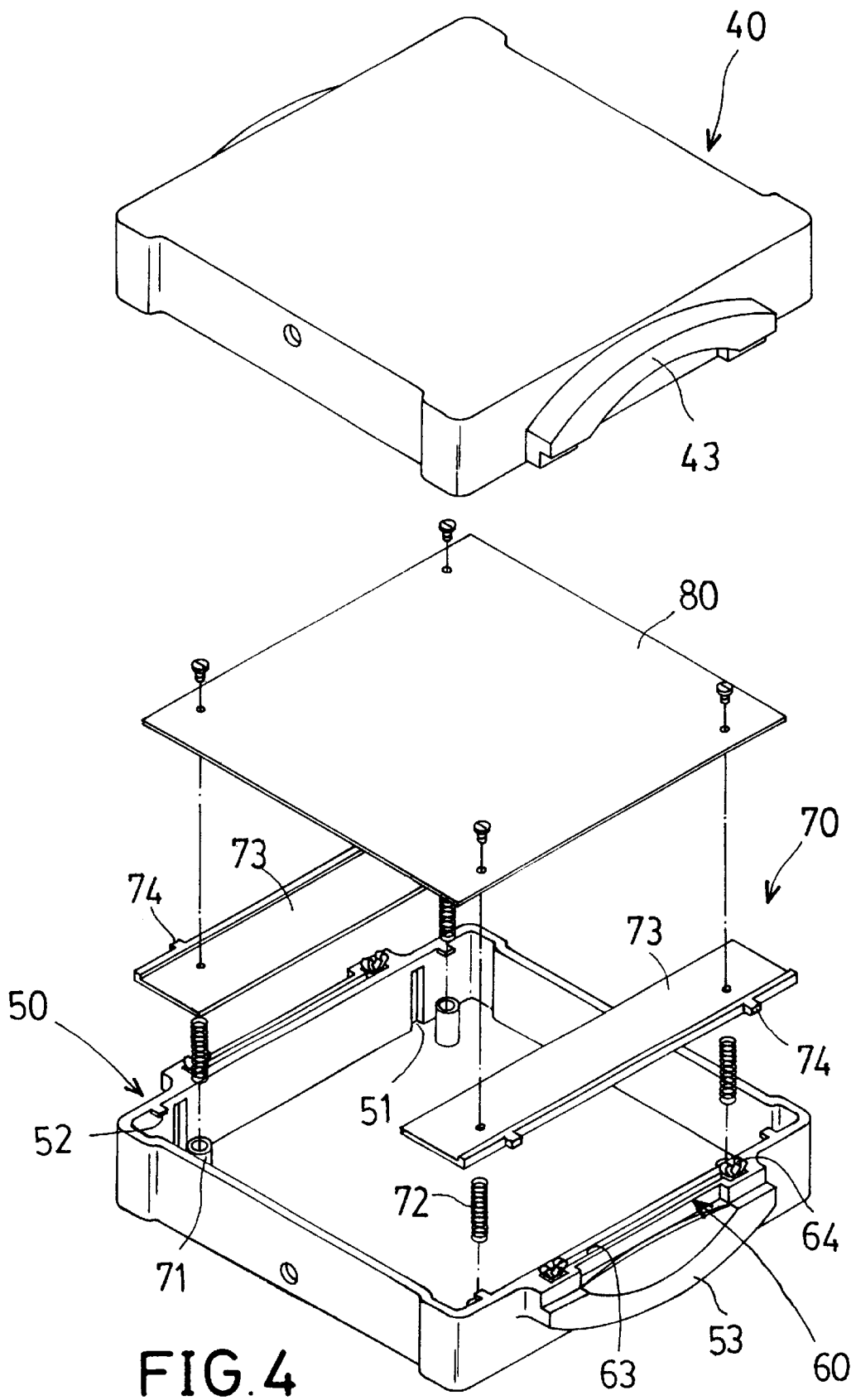
FIG. 4 shows the three-dimensional diagram of the disassembled parts of a preferred embodiment of the present invention.
Figure 5:
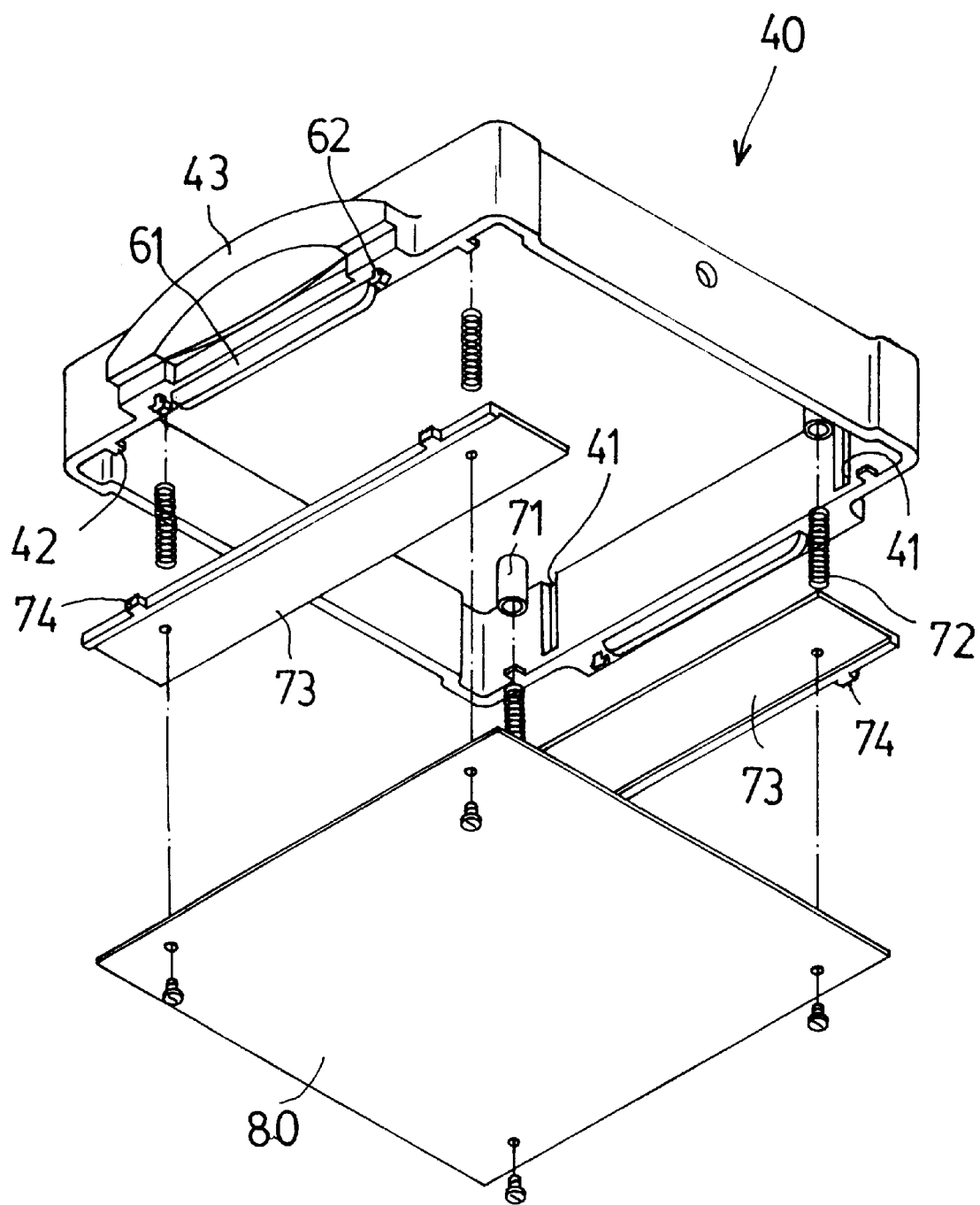
FIG. 5 is the top-view diagram of the disassembled parts of the upper lid of the present invention.
Figure 6:
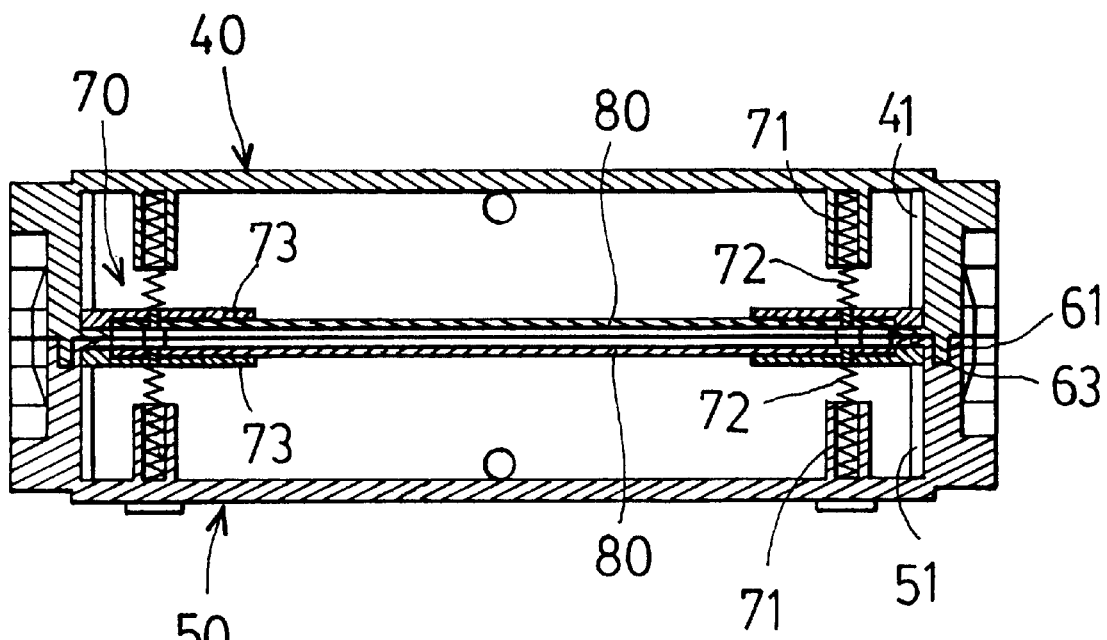
FIG. 6 is the cross-sectional diagram of the electroblotter of the present invention.
Figure 7:
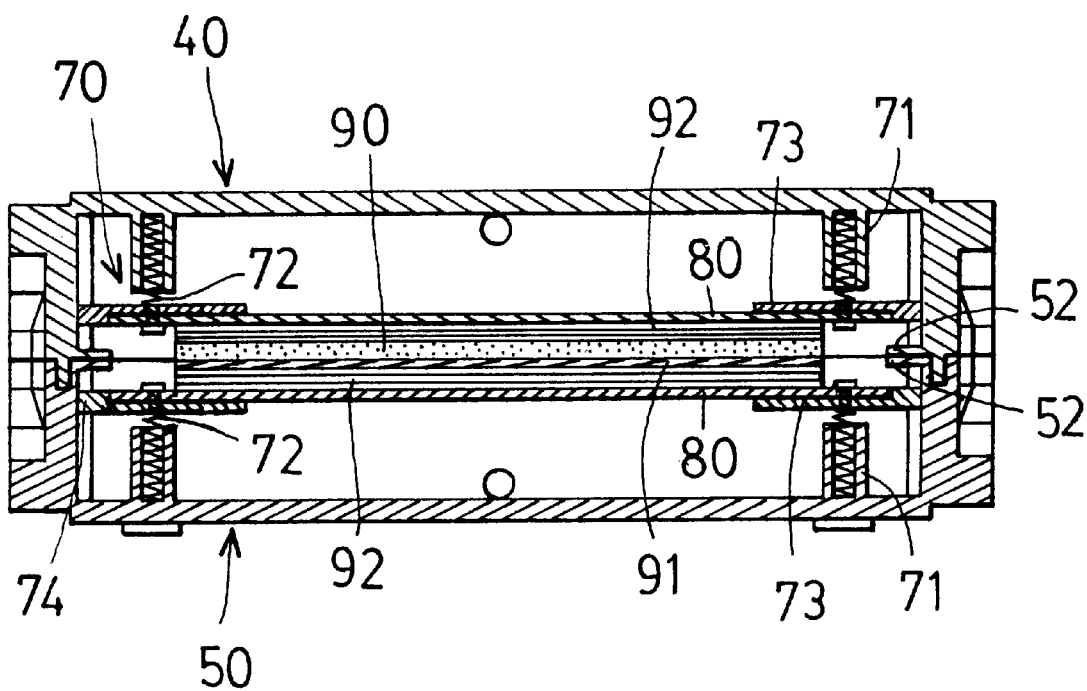
FIG. 7 is the cross-sectional diagram showing the transfer of the electroblotter of the present invention.

Please refer to FIGS. 4 and 5. The electroblotter of the present invention comprises an upper block (40); a corresponding lower block (50); and a corresponding positioning assembly (60) disposed on each of the lateral sides of the upper block (40) and the lower block (50), such that the upper block and the lower block will be coupled automatically when they are closed in a correct guiding position. An elastic member (70) and an electrode plate (80) are separately disposed in the interior of the upper block (40) and the lower block (50), and the elastic member (70) supports the electrode plate (80) so that the electrode plate (80) is biased in the opposite direction when the electrode plate is pressed. When the gel (90), membrane (91), and transfer buffer (92) as shown in FIGS. 6 and 7 are placed on the electrode plate (80) of the lower block (50), and after being covered by the upper block (40), the elastic member (70) will provide an appropriate elastic pressure to the electrode plate (80) of the upper block (40) and the lower block (50) to evenly clamp the gel (90), membrane (91), and transfer buffer (92). When the current passes through the electrode plate for blotting, it can prevent the gel from being damaged or the transfer from being incomplete during the transfer process. The detailed structures of the components are described as follows:

In FIGS. 4 and 5, a plurality of transverse limit grooves (41, 51) and the supporting sections are disposed on the corresponding inner sides of the upper block (40) and the lower block (50); a corresponding handle (43, 53) being disposed on the corresponding outer sides.

Figure 8:
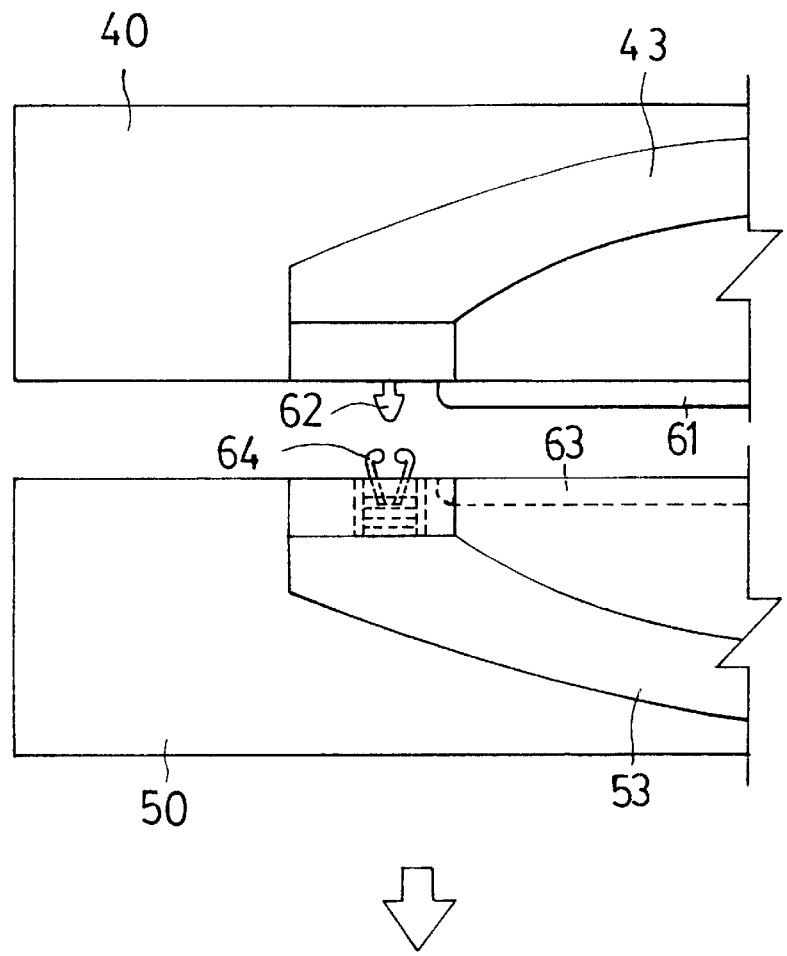
FIG. 8 is the schematic diagram illustrating the coupling status of the upper lid and the lower block of the present invention.
Figure 8:
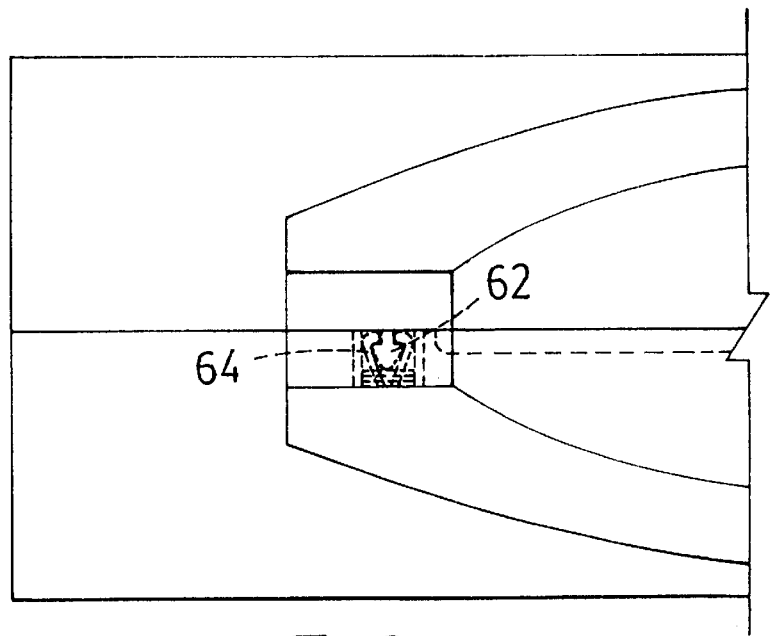

The positioning assembly (60) further comprises a plurality of positioning boards (61), a latching member (62), a groove (63), and a positioning member (64); wherein the positioning board (61) is disposed at the lower section of the inner edge of the handle (43) of the upper block (40); the latching member (62) is disposed at both ends of the positioning board (61); the groove (63) is disposed at the inner edge of the handle (53) of the lower block (50) corresponding to the position of the positioning board (61) for accommodating the positioning board (61) and fixing it in position (please also refer to FIGS. 6 and 7 at the same time); the positioning member (62) being disposed at the position corresponding to the lower block (50) and the latching member (62) so that when the latching member (62) is pressed, it latches the positioning member (64) as shown in FIG. 8.

The elastic member (70) is divided into two parts, each being disposed at the position corresponding to the upper block (40) and the lower block (50), and further comprises a hollow stand (71), an elastic member (72), and a suppressing plate (73). For instance, the elastic member (70) of the lower block (50) as shown in FIG. 4 has a hollow stand (71) disposed at the groove bottom of the lower block (50), and its interior respectively accommodates the elastic member (72) such that the elastic (72) presses on the suppressing plate (73). The plate (73) also include tabs (74) capable of insertion into the limit groove (41, 51) each at a corresponding lateral side of the limit groove (41, 51) of the suppressing plate (73), such that when the suppressing plate (73) slides up and down, it will be guided by the limit groove and will not deviate from its position. In addition, the upper edge of the suppressing plate (73) is located at the lower section of the supporting section (52) of the foregoing lower block (50), so that the supporting section (52) will restrict the height of the suppressing plate (73) and the suppressing plate will not eject from the lower block (50). The elastic member (70) at the upper block (40) as shown in FIG. 5 is disposed upside down relative to the position shown in FIG. 4. It will not be described here.

In FIGS. 4 and 5, the electrode plate (80) in the upper block (40) and the lower block (50) is fixed to the suppressing plate (73) inside the upper block (40) and the lower block (50).

As shown in FIG. 7, when the electroblotter of the present invention proceeds with the gel (90) transfer by the above-mentioned components, the lower section of the gel is stacked with a membrane (91), and the gel (90) and the membrane (91) are wrapped with several layers of transfer buffers (92), and then are placed on the electrode plate (80) of the lower block (50). After the upper block (40) and the lower block (50) are closed, the two sets of upper and lower elastic member (70) will provide an appropriate force to clamp the gel (90), membrane (91), and the transfer buffer (92) evenly by the electrode plate (80) of the upper block (40) and the lower block (50) in order to prevent the gel (90) from being damaged or cracked. Meanwhile, the preferred arrangement also can prevent air bubbles which may give rise to insufficient conductivity when the gel (90), membrane (91), and the transfer buffer (92) are stacked. Such arrangement assures the definite and complete transfer of the molecular mark from the gel onto the membrane (91) after electricity passes through the electrode plate (80). It can prevent the gel from being damaged or having incomplete transfer during electroblotting.

Please refer to FIGS. 6 and 7, when the electroblotter proceeds with the transfer, the elastic member (70) of the upper block (40) and the lower block (50) respectively supports the upper and lower electrode plates (80) such that the electrode plate (80) will have an opposition reaction force when it is pressed. Therefore, when the electrode plate (80) is pressed, the elastic member (72) is compressed, and the protruding tab (74) of the suppressing plate (73) will move within the limit groove (41) and allow the electrode plate (80) to move upward and downward steadily.

Referring to FIG. 8, the foregoing upper block (40) and lower block (50) has a handle (43, 53) each on their lateral sides, wherein the positioning board (61) at the inner side of the handle (43) of the upper block (40) can be inserted into the groove (63) of the lower block (50), and the latching member (62) on both of its ends latches the positioning member (64) of the lower block (50).

When the upper block (40) and the lower block (50) are coupled to each other, the positioning board (61) is inserted into the groove (63) and latching by the latching member (62) and the positioning member (64) can fix them into position. When the latching member (62) and the positioning member are coupled to each other, latching is carried out by pressing the upper block (40) towards the lower block (50). When the upper block (40) and the lower block (50) are separated, the upper block (40) just needs to be evenly pressed downward again, such that the latching member (62) at the lateral side of the upper block (62) is detached from the latch of the positioning member (64), and the upper block (40) and the lower block (50) will be separated providing an easy way to close and open the electroblotter.

From the above FIGS. 4 to 8 and the corresponding description, the upper block (40) and the lower block (50) make use of the coupling between the position board (61) and the groove (63) and the latching between the latching member (62) and the positioning member (64) to attain the purpose of coupling the upper block and the lower block of the electroblotter in a quick fashion. The electrode plate (80) and the suppressing plate (73) can be restricted by the limit groove (41), supporting section (52), and the protruding tab (74). The preferred arrangement allows the gel (60) to have a steady transfer operation, and assures the definite and complete transfer of the mark onto the membrane (91). In addition, since when the electroblotter of the present invention proceeds with the transfer process, it prevents the clamped gel from producing an air bubble when it is pressed by means of the elastic contraction and expansion of the elastic member (72) and also prevents incomplete transfer due to insufficient conductivity, as well as preventing the gel (90) from being damaged by overpressing.

In summation of the above description, the structure of the present invention definitely attains the expected result and effect, enhances the performance of the conventional structure, and further complies with the patent application requirements and it is submitted to the Patent and Trademark Office for review and granting of the commensurate patent rights.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A semi-dry electroblotter, comprising an upper block; a lower block, positioning assemblies including a respective positioning board disposed on lateral sides of the upper block and the lower block, such that the upper block and the lower block are coupled automatically when they are closed in a correct guiding position; and an elastic member and an electrode plate separately disposed in the interior of each of the tipper block and tile lower block, wherein a respective said elastic member supports each electrode plate and biases the respective electrode plate in a clamping direction when a gel, a membrane, and a transfer buffer are placed on the electrode plate in the lower block, covered with the upper block, and thereafter automatically coupled by the positioning boards, and wherein the elastic members provide an appropriate elastic pressure against the electrode plates to cause the respective electrode plates of the upper block and the lower block to evenly clamp the gel, membrane, and transfer buffer; thereby preventing the gel from being damaged or the transfer from being incomplete when current passes through the electrode plate for blotting during the transfer process.

2. A semi-dry electroblotter as claimed in claim 1, wherein said upper block and lower block have two pairs of corresponding handles on both lateral sides, and each positioning assembly further comprises a plurality of fixing plates, latching members, grooves, and positioning members; wherein the positioning board is disposed at the lower section of the inner edge of the handle of the upper block and the latching, members are disposed on both ends of the positioning board and at positions corresponding to a position of the positioning board for accommodating the positioning board; the positioning members being disposed at a position relative to that of the lower block and the latching member such that when the latching member is pressed downward, it is latched to the positioning member; and such that when the transfer is completed, even pressing of the upper block downward will cause the latching member on the lateral side of the upper block to press on the positioning member, and separate the latching member from the latch of the positioning member, and hence separate the upper block and the lower block in order to provide an easy way to open and close the electroblotter.

3. A semi-dry electroblotter as claimed in claim 1, wherein said lower block further comprises a limit groove, a plurality of hollow posts, elastic members, and a suppressing plate; the hollow posts being disposed at the bottom of the lower block, and the elastic members being accommodated in the interior of the hollow posts such that the elastic members support the suppressing plate; a protruding tab being disposed in the limit groove so that the suppressing plate slides up and down, the tab being guided by the limit groove, and presses against the top of the suppressing plate for fixing the electrode plate in position; and such that the upper section of the suppressing plate is supported by the lower section of the lower block and the elastic member presses against the suppressing plate so that the supporting section restricts the height of the suppressing plate and prevents the suppressing plate and the electrode plate from being ejected upward from the lower block as a result of the pressing force provided by the elastic members.

* * * * *